United States Patent
Schmidt et al.

(12)

(10) Patent No.: US 6,482,905 B1
(45) Date of Patent: Nov. 19, 2002

(54) UNSYMMETRIC UNBRIDGED BIS-INDENYL METALLOCENES AND THEIR USE

(75) Inventors: Roland Schmidt, Bartlesville, OK (US); Matthias Deppner, Mistelbach; Helmut G. Alt, Bayreuth, both of (DE); M. Bruce Welch, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/604,021

(22) Filed: Jun. 26, 2000

Related U.S. Application Data

(60) Provisional application No. 60/149,135, filed on Aug. 16, 1999.

(51) Int. Cl.⁷ ................................................ C08F 4/44
(52) U.S. Cl. ...................... 526/160; 556/51; 556/52; 526/170; 526/943; 526/351; 526/352
(58) Field of Search ................... 526/160, 170, 526/943; 556/11, 53, 51, 52; 502/117

(56) References Cited

U.S. PATENT DOCUMENTS

| | | | | |
|---|---|---|---|---|
| 5,071,808 A | | 12/1991 | Antberg et al. ............. 502/107 |
| 5,223,467 A | | 6/1993 | Razavi ....................... 502/152 |
| 5,594,080 A | * | 1/1997 | Waymouth et al. ......... 526/126 |
| 5,646,322 A | * | 7/1997 | van Beek et al. ............. 556/11 |
| 5,719,241 A | | 2/1998 | Razavi et al. ............... 526/119 |
| 5,780,659 A | * | 7/1998 | Schmidt et al. ............... 556/11 |
| 5,854,363 A | * | 12/1998 | Jung et al. .................. 526/160 |
| 5,886,202 A | * | 3/1999 | Jung et al. .................... 556/11 |
| 6,291,699 B1 | * | 9/2001 | Birmingham et al. ....... 556/489 |

FOREIGN PATENT DOCUMENTS

EP  372 414 A2  * 12/1989  ........... C07F/17/00

OTHER PUBLICATIONS

Licht, E.H.; Alt, H.G.; Karim, M.M. J. Organomet. Chem. 2000, 599, 275.*

Kravchenko, R.; Masood, A.; Waymouth, R.M. Organometallics 1997, 16, 3635.*

* cited by examiner

*Primary Examiner*—David W. Wu
(74) *Attorney, Agent, or Firm*—McDermott, Will & Emery

(57) ABSTRACT

Unsymmetrical unbridged bis-substituted indenyl compounds in which one indenyl is substituted by a 2-aryl or 2-aryl alkyl substituent and the other indenyl is substituted by a terminally unsaturated alkenyl or alkyl substituent in the 1 or 2 position and their use in the polymerization of olefins.

19 Claims, No Drawings

UNSYMMETRIC UNBRIDGED BIS-INDENYL METALLOCENES AND THEIR USE

This application is related to Provisional Application Ser. No. 60/149,135, filed Aug. 16, 1999, the disclosure of which is incorporated herein by reference.

This invention relates to specific types of metallocenes. In another aspect, this invention relates to the polymerization of olefins using such metallocenes.

It has been recognized that varying the substituents of metallocenes can affect the manner in which the materials act as catalysts in the polymerization of olefins. The present invention is based upon the discovery of a new class of unbridged metallocenes that are suitable for use as catalysts in the polymerization of olefins.

SUMMARY OF THE INVENTION

The present invention concerns an unbridged metallocene of a transition metal selected from the group consisting of zirconium, titanium, and hafnium having two substituted indenyl groups, one indenyl group being substituted in the 2 position by an aromatic substituent selected from phenyl and phenyl alkyl radicals in which there are 1 to 3 carbon atoms between the phenyl group and the indenyl group, and the other indenyl group being substituted in either the 1 position or 2 position by a non-aromatic substituent selected from alkyl groups having 2 to 6 carbon atoms and terminally unsaturated alkene groups having 2 to 6 carbon atoms. The invention is also directed to using such metallocenes in the polymerization of olefins.

DETAILED DESCRIPTION OF THE INVENTION

In order to prepare the metallocenes of this invention, it is necessary to prepare the corresponding substituted indene compounds. The preparation of indene compounds having an aryl, aryl alkyl, or alkyl group in the 2 position can be carried out by reacting a selected alkyl, aryl, or aryl alkyl Grignard reagent or an alkyl bromide with 2-indanone. The resulting product can then be hydrolyzed to obtain an alcohol intermediate. The intermediate can then be reacted with p-toluenesulfonic acid monohydrate to effect dehydration and subsequent production of the desired substituted indenyl.

Indene compounds substituted with terminally unsaturated alkenyl or alkyl groups in the 1 position can be readily produced by reacting a suitable alkyl or alkenyl bromide to the lithium salt of indene.

It is not considered practical to prepare the unsymmetric unbridged bis-indenyl metallocenes of the present invention by merely combining the alkali metal complexes of the two different indenyls with a transition metal halide. The presently preferred method for preparing such metallocenes instead involves contacting the 2-substituted indenyl with tributyltin chloride to produce an intermediate having tributyltin at the 1 position. That product is then reacted with a transition metal tetrahalide to produce a 2-substituted half-sandwich type metallocene. This can be referred to as a 2-substituted indenyl transition metal trichloride complex. The indenyl transition metal trichloride complex is then reacted with the lithium salt of the other substituted indene to obtain the desired metallocene.

The inventive metallocenes can be used in combination with a suitable cocatalyst for the polymerization of olefinic monomers. In such processes the metallocene and/or cocatalyst can be employed in combination with a solid insoluble particulate carrier. It is also within the scope of the present invention to carry out a prepolymerization to obtain a prepolymerized catalyst system.

Examples of cocatalysts which could be used with the metallocenes include generally any of those which in the past have been used with metallocene olefin polymerization catalysts. Some typical examples include tris (perfluorophenyl) borane and related compounds and organometallic compounds of Groups IA, IIA, and IIIB of the Periodic Table. Examples of such organometallic compounds have included organometallic halide compounds, organometallic hydrides, and even metal hydrides. Some specific examples include triethylaluminum, triisobutylaluminum, diethylaluminum chloride, diethylaluminum hydride, and the like. It is also possible to use as the cocatalyst materials produced by reacting a support with a trialkyl aluminum and water such as disclosed in U.S. Pat. No. 5,900,035.

The currently most preferred cocatalyst is an aluminoxane. Aluminoxanes, also sometimes referred to as poly (hydrocarbyl aluminum oxide) are well known in the art and are generally prepared by reacting an organo hydrocarbon aluminum compound with water.

The currently preferred aluminoxanes are those prepared from either trimethylaluminum or triethylaluminum. It is within the scope of the invention to use solid forms of aluminoxane. One such example would be the solid aluminoxanes such as disclosed in U.S. Pat. No. 5,354,721.

The metallocenes can be used to polymerize olefins, especially alpha olefins having 2 to 12 carbon atoms. Such polymerizations can be carried out in solution polymerization conditions as well as slurry or gas phase polymerization conditions. It is further within the scope of the invention to use a mixture of two or more of the inventive metallocenes or a mixture of one of the inventive metallocenes and one or more other metallocenes.

The metallocenes are particularly useful in the polymerization of ethylene in the presence of or absence of other olefins. Examples of other olefins that could be used as comonomers with ethylene include alpha olefins having 3 to 10 carbon atoms. Some such olefins include propylene, butene-1, pentene-1, 3-methylbutene-1, hexene-1, 4-methylpentene-1, 3-methylpentene-1, heptene-1, octene-1, decene-1, and the like and mixtures thereof.

Polymerizations can be carried out under a wide range of conditions depending upon the particular metallocene employed and the results desired. The amount of cocatalyst can vary over a wide range. It is currently preferred for the molar ratio of the aluminum in the aluminoxane to the transition metal in the metallocene to be in the range of about 0.1:1 to about 100,000:1 and more preferably about 5:1 to about 15,000:1. In many cases it is desirable to carry out the polymerization in the presence of liquid diluents which do not have an adverse affect upon the catalyst system. Some such diluents include propane, butane, isobutane, pentane, hexane, heptane, octane, cyclohexane, methyl cyclohexane, toluene, xylene, and the like. The polymerization temperature can vary over wide range. Temperatures would typically be in the range of from about $-60°$ C. to about $300°$ C., more preferably in the range of about $20°$ C. to about $300°$ C. Typically the pressure would be in the range of from about 2 to 500 atmospheres.

The polymers produced with this invention have a wide range of uses that will be apparent to those skilled in the art from the physical properties of the produced polymers.

A further understanding of the present invention and its advantages will follow from the following examples.

The 2-alkyl or 2-aryl alkyl substituted indene compounds used in preparing some of the inventive metallocenes were prepared using a Grignard reagent procedure. An example would involve preparing a suspension of 3.37 grams of magnesium chips in 150 mL of diethylether. Then 14 millimoles of the selected aryl alkyl bromide would be added. After about 10 minutes, an additional 125 millimoles of the aryl alkyl bromide dissolved in 100 mL of diethylether would be added dropwise followed by stirring for about 2 hours. Then 16.5 grams of 2-indanone dissolved in 150 mL of diethylether would be slowly added. The stirring would be continued for some period such as overnight. Then the mixture would be hydrolyzed with a 1–5 molar hydrochloric acid solution at 0° C. The resulting organic layer would then be separated and washed twice with a sodium hydrocarbonate solution and dried over sodium sulfate. The solvent would then be removed. The resulting recovered alcohol compound would then be dissolved in 250 mL of toluene and 10 millimoles of p-toluenesulfonic acid monohydrate would be added. The mixture would be refluxed until the formed water had separated in a Dean-Stark apparatus. After cooling to room temperature, the mixture would be washed with sodium hydrocarbonate solution. The organic layer would then be dried over sodium sulfate and the solvent removed by vacuum. The desired indene derivatives would then be recovered by crystallization.

The general procedure for preparing a 1-omega-alkenyl substituted indene or a 1-alkyl substituted indene would be to dissolve 10 mL of indene in 150 mL of diethylether and 15 mL of tetrahydrofuran. Then an equal molar amount of a 1.6 molar n-hexane solution of n-butyllithium would be added dropwise at about −78° C. After stirring at room temperature for about 5 hours, the solution would be cooled to −78° C. and an equal molar amount of the selected omega-alkenyl bromide or alkyl bromide would be added. The resulting mixture would then be stirred overnight and hydrolyzed with water. The organic layer would be separated and dried over sodium sulfate, the solvent would be evaporated, and the product recovered.

The general procedure for producing the inventive mixed metallocenes involves first preparing a 1-tributyl stannyl indene derivative. For example, 12 millimoles of the desired indene would be dissolved in 150 mL of diethylether and an equal molar amount of a 1.6 molar n-hexane solution of n-butyllithium would be added dropwise at −78° C. After stirring at room temperature for several hours and recooling to −78° C., tributyltin chloride would be added. Stirring would be continued overnight at room temperature. The solvent would then be evaporated and the residue suspended in n-pentane. The suspension would be filtered through sodium sulfate and then solvent evaporated from the filtrate.

The half-sandwich metallocene would be prepared by preparing a suspension of 5.17 grams of zirconium tetrachloride in 150 mL of toluene. Then a solution of an equal molar amount of the 1-tributyl stannyl indene derivative dissolved in 80 mL of toluene would be added. The mixture would be stirred overnight then filtered and washed with n-pentane. Then the solvent would be evaporated.

Finally to prepare the inventive unsymmetrical unbridged bis-indenyl metallocenes, one would add to 4.1 millimoles of an alkyl or omega-alkenyl substituted indene derivative, dissolved in 150 mL of diethylether, and 2.6 mL of a 1.6 molar n-hexane solution of n-butyllithium at −78° C. The mixture would be stirred for several hours. The mixture would then be again cooled to −78° C. and the desired half-sandwich compound would be added in an equal molar amount. After stirring overnight and evaporation of the solvent, the residue would be extracted with methylene dichloride. The suspension would be filtered over sodium sulfate. The solvent would then be evaporated from the filtrate and the resulting metallocene recrystallized from toluene at −78° C.

These general techniques were used to prepare the metallocenes that were later used in the polymerization processes to now be discussed. Ethylene polymerizations were carried out by combining the metallocene with methylaluminoxane to give an aluminum to zirconium ratio of 3000:1. The ethylene was applied into the reactor at 10 bar. The slurry polymerization in 500 mL of n-pentane was carried out at 60° C.

The polymerizations of propylene were carried out as bulk polymerization in 500 mL of liquid propylene at 0° C. Again an aluminum to zirconium ratio of 3000:1 was used with methylaluminoxane as the cocatalyst.

The results of the ethylene polymerizations using the inventive catalysts are summarized in the following Table I.

TABLE I

| Catalyst precursor | | productivity in g(PE)/g(Zr).h$^{-1}$ | $\overline{M}_w$ in g/mol | polydispersity |
|---|---|---|---|---|
| 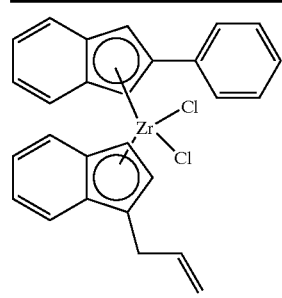 | 1 | 118,200 | 1,065,000 | 4.76 |
| 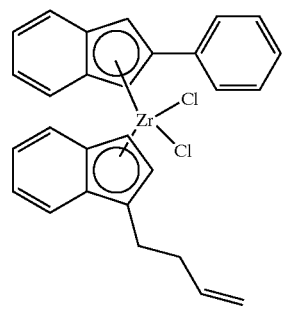 | 2 | 70,000 | 884,200 | 5.14 |

TABLE I-continued
| Catalyst precursor | productivity in g(PE)/g(Zr).h$^{-1}$ | $\overline{M}_w$ in g/mol | polydispersity |
|---|---|---|---|
| 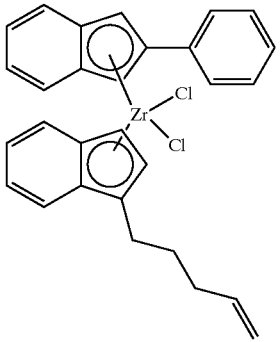 3 | 193,100 | 1,044,000 | 3.73 |
| 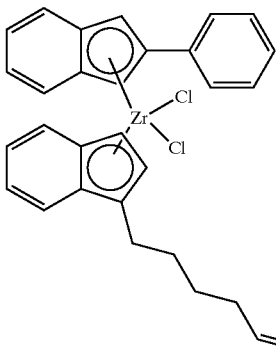 4 | 59,400 | 814,900 | 3.27 |
| 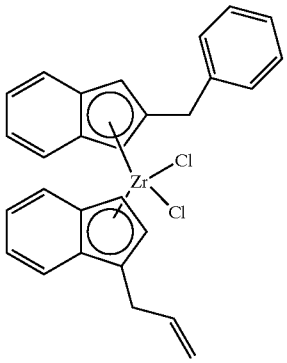 5 | 40,000 | 459,100 | 10.12 |
| 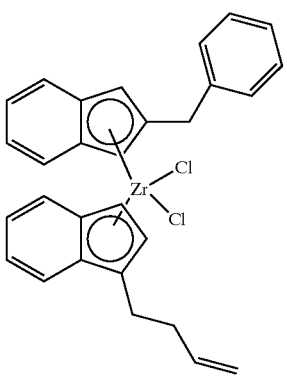 6 | 151,000 | 1,120,000 | 4.55 |

TABLE I-continued
| Catalyst precursor | | productivity in g(PE)/g(Zr).h$^{-1}$ | $\overline{M}_w$ in g/mol | polydispersity |
|---|---|---|---|---|
| 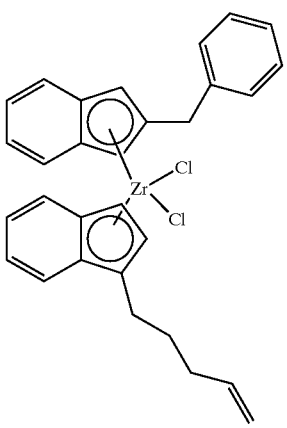 | 7 | 198,300 | 835,100 | 5.78 |
| 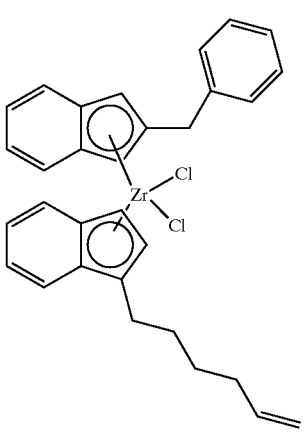 | 8 | 191,000 | 882,400 | 7.41 |
| 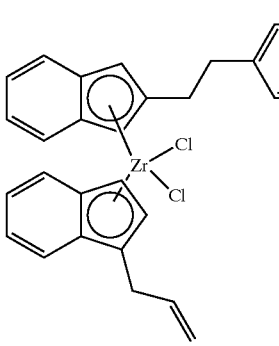 | 9 | 123,900 | 1,049,000 | 5.83 |
| 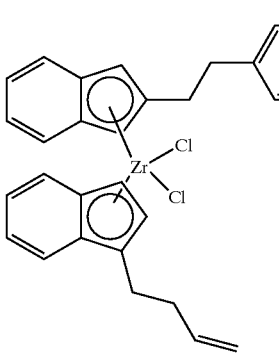 | 10 | 200,800 | 1,084,000 | 4.22 |

TABLE I-continued

| Catalyst precursor | | productivity in g(PE)/g(Zr).h$^{-1}$ | $\overline{M}_w$ in g/mol | polydispersity |
|---|---|---|---|---|
| | 11 | 249,400 | 1,071,000 | 8.64 |
| | 12 | 151,000 | 989,000 | 4.13 |
| | 13 | 150,600 | 1,120,000 | 9.23 |
| | 14 | 112,000 | 1,022,000 | 6.80 |

TABLE I-continued

| Catalyst precursor | | productivity in g(PE)/g(Zr).h$^{-1}$ | $\overline{M}_w$ in g/mol | polydispersity |
|---|---|---|---|---|
| *(structure)* | 15 | 156,300 | 1,258,000 | 3.94 |
| *(structure)* | 16 | 180,100 | 1,135,000 | 9.12 |
| *(structure)* | 17 | 40,200 | 522,100 | 3.70 |
| *(structure)* | 18 | 89,600 | 949,000 | 19.86 |

TABLE I-continued
| Catalyst precursor | | productivity in g(PE)/g(Zr).h⁻¹ | $\overline{M}_w$ in g/mol | polydispersity |
|---|---|---|---|---|
| 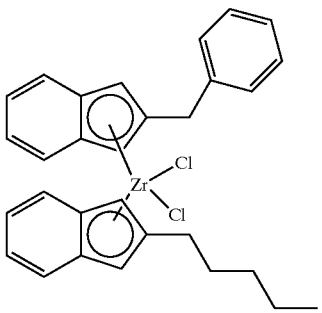 | 19 | 136,800 | 1,692,000 | 4.98 |
| 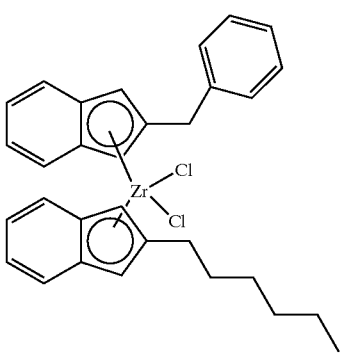 | 20 | 85,400 | 963,000 | 23.33 |
| 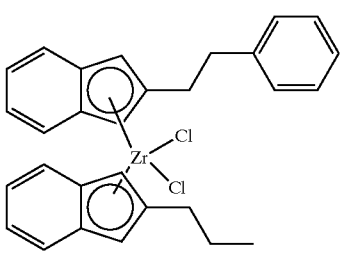 | 21 | 115,900 | 1,202,000 | 6.01 |
| 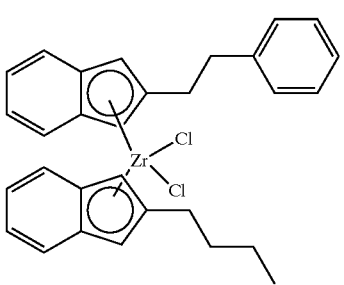 | 22 | 115,400 | 1,175,000 | 5.27 |
| 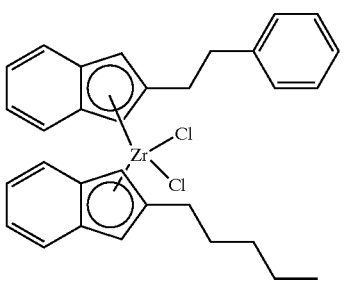 | 23 | 75,800 | 123,700 | 2.76 |

TABLE I-continued

| Catalyst precursor | | productivity in g(PE)/g(Zr).h⁻¹ | $\overline{M}_w$ in g/mol | polydispersity |
|---|---|---|---|---|
| [structure: bis(indenyl)ZrCl₂ with 2-phenethyl and pentyl substituents] | 24 | 105,400 | 964,100 | 5.50 |
| [structure: bis(indenyl)ZrCl₂ with 2-phenethyl and butyl substituents] | 25 | 176,000 | 667,200 | 5.94 | a)Polymerization parameters: Polymerization in n-pentane; at 60° C.; 60 minutes, Al/Zr ratio: 3.000/1.

The results demonstrate that the different metallocenes produce catalysts of differing activity and produce polymers of different molecular weights. Mixtures of such metallocenes could thus be used to produce polymers having broader molecular weight distributions, in some cases multimodal molecular weight distributions.

The most active catalysts in ethylene polymerization were Catalyst 7, i.e. (2-phenylmethyl indenyl) (1-(4-pentenyl) indenyl)zirconium dichloride, and Catalysts 8, 10, 11, 16, and 25.

The results of the propylene polymerization are summarized in the following Table II.

TABLE II

| Catalyst precursor | | productivity in g(PP)/g(Zr).h⁻¹ | $\overline{M}_w$ in g/mol | polydispersity |
|---|---|---|---|---|
| [structure: bis(indenyl)ZrCl₂ with 2-phenyl and allyl substituents] | 1 | 1.6 | 2,278,000 | 27.38 |
| [structure: bis(indenyl)ZrCl₂ with 2-phenyl and 3-butenyl substituents] | 2 | 1.4 | 24,790,000 | 341.6 (bimodal) |

TABLE II-continued
| Catalyst precursor | | productivity in g(PP)/g(Zr).h$^{-1}$ | $\overline{M}_w$ in g/mol | polydispersity |
|---|---|---|---|---|
| 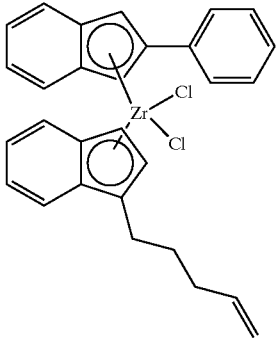 | 3 | 2.5 | 280,500 | 2.67 |
| 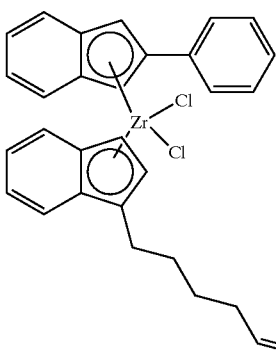 | 4 | 3.1 | 281,100 | 3.1 |
| 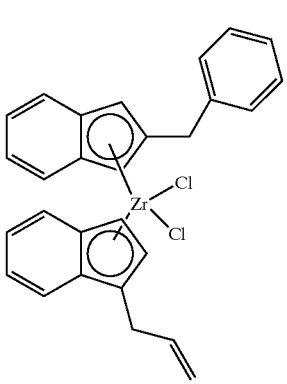 | 5 | 2.9 | 665,800 | 8.2 |
| 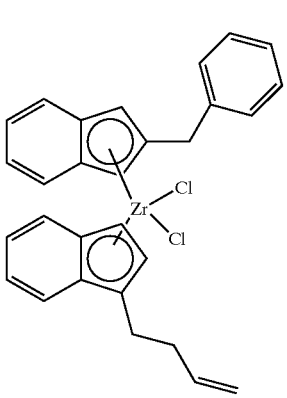 | 6 | 5 | 177,400 | 2.49 |

TABLE II-continued
| Catalyst precursor | productivity in g(PP)/g(Zr).h$^{-1}$ | $\overline{M}_w$ in g/mol | polydispersity |
|---|---|---|---|
| 7 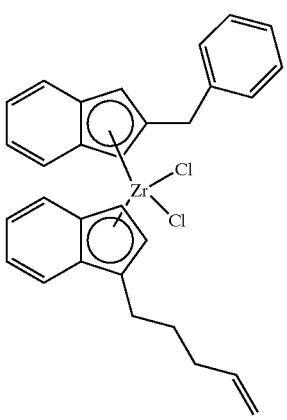 | 8 | 657,000 | 4.61 |
| 8 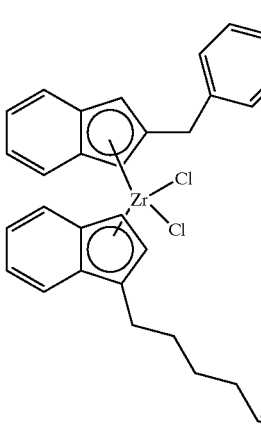 | 6.4 | 138,400 | 2.24 |
| 9 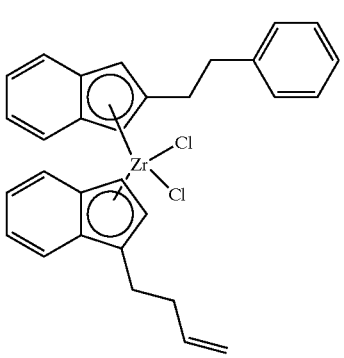 | 4.8 | 477,800 | 5.4 |
| 10 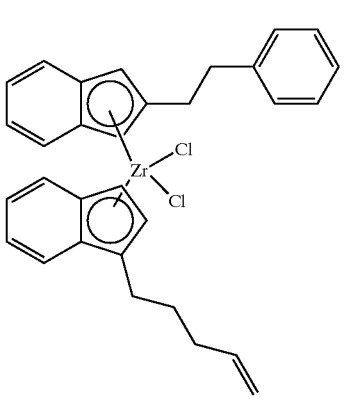 | 1.2 | 534,600 | 8.98 (bimodal) |

TABLE II-continued
| Catalyst precursor | | productivity in g(PP)/g(Zr).h$^{-1}$ | $\overline{M}_w$ in g/mol | polydispersity |
|---|---|---|---|---|
| 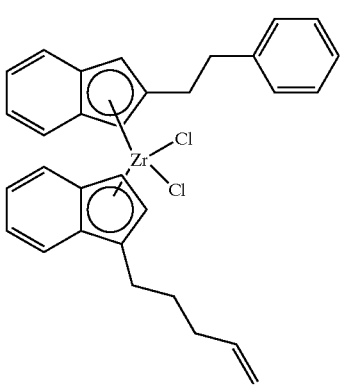 | 11 | 3 | 336,000 | 3.47 |
| 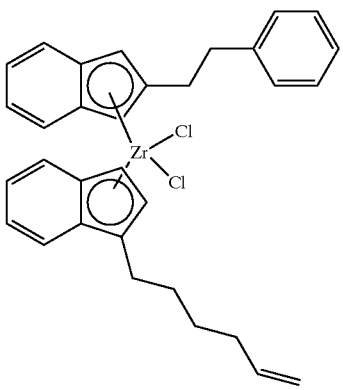 | 12 | 3.1 | 342,500 | 4.66 |
| 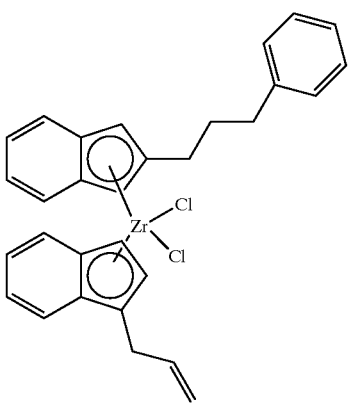 | 13 | 3.4 | 968,100 | 4.99 |
| 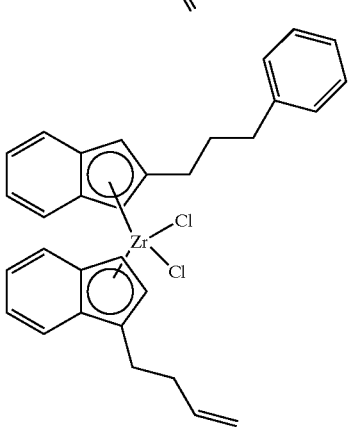 | 14 | 2.4 | 228,400 | 10.91 |

TABLE II-continued

| Catalyst precursor | | productivity in g(PP)/g(Zr).h⁻¹ | $\overline{M}_w$ in g/mol | polydispersity |
|---|---|---|---|---|
| | 15 | 4.9 | 509,400 | 9.83 (bimodal) |
| | 16 | 3.7 | 470,300 | 3.87 (bimodal) |
| | 17 | 18.8 | 563,800 | 6.04 |
| | 18 | 41.1 | 370,500 | 6.17 |

TABLE II-continued

| Catalyst precursor | productivity in g(PP)/g(Zr).h$^{-1}$ | $\overline{M}_w$ in g/mol | polydispersity |
|---|---|---|---|
| 19 | 36.4 | 736,300 | 2.66 |
| 20 | 31.6 | 587,200 | 3.59 |
| 21 | 62.8 | 913,000 | 142.5 (bimodal) |
| 22 | 64 | 546,300 | 9.55 |
| 23 | 60.1 | 3,806,000 | 81.62 (bimodal) |

TABLE II-continued

| Catalyst precursor | | productivity in g(PP)/g(Zr).h$^{-1}$ | $\overline{M}_w$ in g/mol | polydispersity |
|---|---|---|---|---|
| 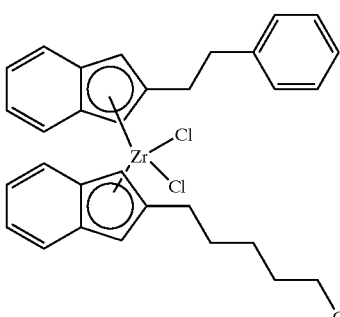 | 24 | 57.4 | 1,095,000 | 12.92 |
| 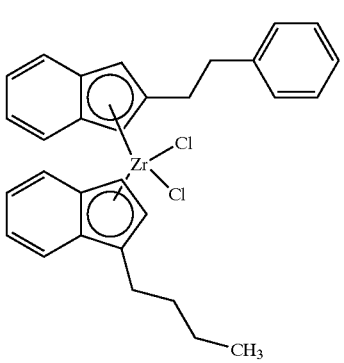 | 25 | 13 | 537,900 | 5.56 |

$^{a)}$Polymerization parameters: bulk polymerization in 500 ml liquid propene at 0° C.; Al/Zr ratio: 3.000/1.

The most active catalysts for propylene polymerization were Catalysts 23 and 24. Those catalysts also produced the highest molecular weight polymer.

That which is claimed is:

1. An unbridged metallocene of a transition metal selected from the group consisting of zirconium, titanium, and hafnium having two substituted indenyl groups, one indenyl group being substituted in the 2 position by an aromatic substituent selected from phenyl and phenyl alkyl radicals in which there are 1 to 3 carbon atoms between the phenyl group and the indenyl group, and the other indenyl group is substituted in either the 1 position or 2 position by a non-aromatic substituent selected from alkyl groups having 2 to 6 carbon atoms and terminally unsaturated alkene groups having 2 to 6 carbon atoms.

2. A metallocene according to claim 1 wherein the transition metal is zirconium.

3. A metallocene according to claim 2 wherein 1-indenyl is substituted by a terminally unsaturated alkenyl radical.

4. A metallocene according to claim 3 wherein the phenyl alkyl group is phenyl ethyl.

5. A metallocene according to claim 4 wherein the alkenyl group is 4-pentenyl.

6. A metallocene according to claim 3 wherein the alkenyl group is 3-butenyl.

7. A metallocene according to claim 3 wherein the phenyl alkyl group is phenyl methyl.

8. A metallocene according to claim 7 having an indenyl group substituted in the 1 position by 4-pentenyl.

9. A metallocene according to claim 7 having an indenyl group substituted in the 1 position by 5-hexenyl.

10. A metallocene according to claim 2 having an indenyl group substituted by phenyl methyl.

11. A metallocene according to claim 10 having an indenyl group substituted in the 2 position by an alkyl substituent.

12. A metallocene according to claim 11 having an indenyl group substituted in the 2 position by 1-pentyl.

13. A metallocene according to claim 2 having an indenyl group substituted by phenyl ethyl.

14. A metallocene according to claim 13 having an indenyl group substituted in the 2 position by an alkyl group.

15. A metallocene according to claim 14 having an indenyl substituted in the 2 position by an alkyl group having 5 to 6 carbon atoms.

16. A process for polymerizing an olefin comprising contacting the olefin under suitable polymerization conditions with a metallocene according to claim 1 and a suitable cocatalyst.

17. A process according to claim 14 wherein ethylene is polymerized.

18. A process according to claim 16 wherein propylene is polymerized.

19. A process according to claim 18 wherein said metallocene is selected from the group consisting of (2-phenylethyl indenyl) (2-n-pentylindenyl) zirconium dichloride and (2-phenylethyl indenyl) (2-n-hexylindenyl) zirconium dichloride.

* * * * *